United States Patent [19]
Scott

[11] Patent Number: 5,208,355
[45] Date of Patent: May 4, 1993

[54] COSMETIC COMPOSITION

[75] Inventor: Ian R. Scott, Wellingborough, England

[73] Assignee: Chesebrough-Pond's USA Co., Division of Conopco, Inc., Greenwich, Conn.

[21] Appl. No.: 693,883

[22] Filed: May 1, 1991

[30] Foreign Application Priority Data

May 1, 1990 [GB] United Kingdom ............... 9009793

[51] Int. Cl.$^5$ ........................................... C07C 251/00
[52] U.S. Cl. ........................................ 554/37; 554/40; 554/61; 554/63; 554/64; 554/66; 554/68; 554/69
[58] Field of Search ................... 554/37, 40, 61, 63, 554/64, 66, 68, 69; 514/563, 612, 873

[56] References Cited

U.S. PATENT DOCUMENTS 4,950,688  8/1989  Bowser et al. .................. 514/847

FOREIGN PATENT DOCUMENTS 0097059 12/1983 European Pat. Off. .
227994  7/1984 European Pat. Off. .
0227994  7/1987 European Pat. Off. .
0282816  9/1988 European Pat. Off. .
0398272 11/1990 European Pat. Off. .

OTHER PUBLICATIONS

J. Soc. Cosmet. Chem., 40, pp. 273-285 (Sep./Oct. 1989) "Water—Retaiing Function in the Stratum Corneum and its Recovery Properties by Synthetic Pseudoceramides", Imokawa et al.

Primary Examiner—José G. Dees
Assistant Examiner—Deborah D. Carr
Attorney, Agent, or Firm—Milton L. Honig

[57] ABSTRACT

Novel amide derivatives have the following structure (1):

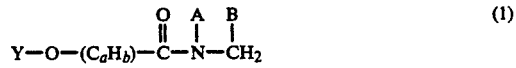

where
Y is hydrogen or an unsaturated fatty acid residue,
A is an hydroxyalkyl group,
B is a sugar or phosphate residue, and
$(C_aH_b)$ is a hydrocarbon residue with from 7 to 49 carbon atoms.

The amide derivative can be employed in compositions, together with a suitable carrier, for topical application, particularly to improve damaged human skin or hair.

7 Claims, No Drawings

COSMETIC COMPOSITION

FIELD OF THE INVENTION

The invention relates to novel ω-acyl-substituted amides, their synthesis and use in composition for topical application to human skin or hair.

BACKGROUND TO THE INVENTION AND PRIOR ART

It is well established that ceramides have a vital role in the production and maintenance of the water permeability barrier of the skin. Ceramides, or substances closely related to them, have been widely disclosed as components of skin care compositions. Of particular interest in this respect is the disclosure by Kao Corporation in EP 0227994 of synthetic analogues of ceramides which, to a significant extent, have similar properties to natural ceramides but which are relatively cheaper to produce.

However, the degree of skin benefit attributable to such natural ceramides or analogues thereof is limited to the extent that they do not fully mimic the natural ceramides of the skin. Unilever NV in EP 0 097 059 disclosed the vital role played by ω-linoleoyl ceramides in the water barrier of the skin and described the synthesis and application for skin care of such ω-substituted ceramides. Application of this latter invention is however limited due to the high cost of synthesis and limited availability of the naturally occurring compounds.

SUMMARY OF THE INVENTION

We have now identified certain specific analogues of naturally occurring ω-acyl-substituted amides which resemble in their key properties the natural substances.

DEFINITION OF THE INVENTION

Accordingly, the invention provides an amide derivative having the structure (1):

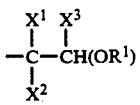
(1)

where Y is H or a residue of an all cis n-6,9 fatty acid or a derivative thereof, having the structure (2):

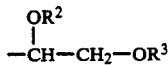
(2)

where
Z is —OH or an epoxy oxygen
x is an integer of from 6 to 20
y is an integer of from 24 to 36, and
z is 0, or an integer of from 1 to 4;
provided that:
when z=0
then y is an integer from 26 to 36 or when z is an integer of from 1 to 4, then y is an integer of from 24 to 35;
and where
a is an integer of from 7 to 49
b is an integer of from 10 to 98
and where A is the group
—$(CH_2)_c$ OH, where c is an integer of from 1 to 6 or $$-\underset{X^2}{\underset{|}{\overset{X^1}{\overset{|}{C}}}}-CH(OR^1) \quad (3)$$

where $X^1$, $X^2$, $X^3$ are individually H, $C_{1-5}$ alkyl or hydroxyalkyl, and $R^1$ is H, a sugar residue or a phosphate residue.
and where B is $$-\underset{}{\overset{OR^2}{\overset{|}{CH}}}-CH_2-OR^3 \quad (4)$$

where
$R^2$ is H, a sugar residue or phosphate residue; and
$R^3$ is a $C_{8-28}$ aliphatic hydrocarbon or the group
—CH(OH) $R^3$ with $R^3$ as defined above.

Particularly preferred examples of the amide derivatives are those having the structures (5), (6) and (7):

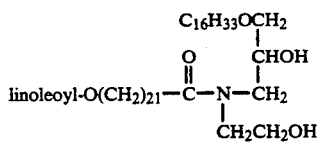
(5)

N-(2-hydroxy-3-hexadecyloxypropyl)-N-
2-hydroxyethyl-ω-0-linoleoyldocosanamide.

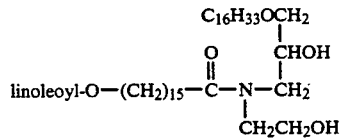
(6)

N-(2-hydroxy-3-hexadecyloxypropyl)-N-
2-hydroxyethyl-ω-0-linoleoylhexadecanamide.

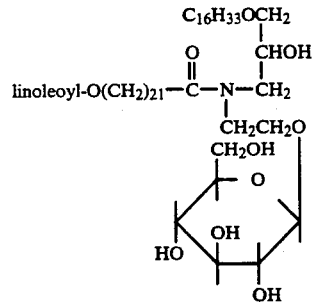
(7)

N-(2-hydroxy-3-hexadecyloxypropyl)-N-
(2-0-glucopyranosyl)ethyl-ω-0-linoleoyldocosanamide

SYNTHESIS OF THE SUBSTITUTED CERAMIDE

The amide derivatives can conveniently be synthesised by first preparing the precursor (8):

(8)

where Y, a and b are as defined herein, by the method described by Unilever NV in EP 0 097 059.

This is converted to the acid chloride and condensed with the amine derivative having the structure (9):

$$\begin{array}{cc} A & B \\ | & | \\ HN-CH_2 \end{array} \qquad (9)$$

where A and B are as defined herein, prepared as described by Kao Corporation in EP 0 282 816, and OH-protected by silylation as described by Unilever NV in EP 0 097 059. After removal of the protecting groups the desired amide derivative having the structure (1) is obtained.

SPECIFIC EXAMPLE OF THE SYNTHESIS

In a preferred embodiment of the invention, Y is a linoleoyl group, $(C_aH_b)$ is a saturated $C_{21}$ alkyl group, A is —$CH_2CH_2OH$ and B is —$CH(OH)CH_2$—O—$C_{16}H_{33}$.

The synthesis is thus represented by:

$$\begin{array}{c} C_{16}H_{33}-O-CH_2 \\ | \\ CH \\ | \quad \backslash \\ | \quad \quad O \\ | \quad / \\ CH_2 \end{array} \xrightarrow[\text{silylation}]{\text{NH}_2\text{CH}_2\text{CH}_2\text{OH} \atop \text{followed by}} \begin{array}{c} C_{16}H_{33}OCH_2 \\ | \\ CHOSi(CH_3)_3 \\ | \\ HN-CH_2 \\ | \\ CH_2CH_2OSi(CH_3)_3 \end{array} \qquad (10)$$

$$HO(CH_2)_{21}COOH \xrightarrow{\text{linoleoyl chloride}} \text{linoleoyl-O}-(CH_2)_{21}COOH \qquad (11)$$

$$\downarrow SOCl_2$$

$$\text{linoleoyl-O}-(CH_2)_{21}COCl$$

Condensation of intermediates (10) and (11) followed by deprotection to remove the two trimethylsilyl ether groups yields the amide derivative having the structure (5), as follows:

$$\begin{array}{c} C_{16}H_{33}OCH_2 \\ | \\ CH-OSi(CH_3)_3 \\ | \\ CH_2 \\ | \\ HN \\ | \\ CH_2CH_2\text{---}OSi(CH_3)_3 \end{array} \qquad (10)$$

$$+$$

$$\text{linoleoyl-O(CH}_2)_{21}COCl \qquad (11)$$

$$\downarrow$$

$$\begin{array}{c} C_{16}H_{33}OCH_2 \\ | \\ O \quad \quad CHOH \\ \| \quad \quad | \\ \text{linoleoyl-O(CH}_2)_{21}-C-N-CH_2 \\ | \\ CH_2CH_2OH \end{array} \qquad (5)$$

N-(2-hydroxy-3-hexadecyloxypropyl)-N-2-hydroxyethyl-ω-0-linoleoyldocosanamide.

DEFINITION OF COMPOSITIONS OF THE INVENTION

The invention also provides a composition for topical application to human skin which comprises:
 i. an effective amount of an amide derivative having the structure (1); and
 ii. a cosmetically acceptable vehicle for the synthetic ceramide.

DISCLOSURE OF THE COMPOSITION

The composition according to the invention comprises in its simplest form a special amide derivative and a vehicle therefor to enable the amide derivative to be dispersed onto the skin and distributed thereon.

THE AMIDE DERIVATIVE

The composition according to the invention comprises an effective amount of an amide derivative having the structure (1) as herein defined.

Preferred examples of the amide derivative having the structure (1) are those where Y is chosen from:
linoleoyl
linolenoyl
γ-linolenoyl
columbinoyl, and
arachidonoyl.

Particularly preferred examples of the amide derivative are those having the structures (5), (6) and (7) as described herein.

The amount of the amide derivative present in the composition according to the invention is from 0.00001 to 50%, preferably from 0.001 to 20% and most preferably from 0.1 to 10% by weight.

THE COSMETICALLY ACCEPTABLE VEHICLE

The composition according to the invention also comprises a cosmetically acceptable vehicle to act as a dilutant, dispersant or carrier for the amide derivative in the composition, so as to facilitate its distribution when the composition is applied to the skin and/or hair.

Vehicles other than water can include liquid or solid emollients, solvents, humectants, thickeners and powders. Examples of each of these types of vehicle, which can be used singly or as mixtures of one or more vehicles, are as follows:

Emollients, such as stearyl alcohol, glyceryl monoricinoleate, glyceryl monostearate, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, tallow, lard, olive oil, palm kernel oil, rapeseed oil, safflower seed oil, evening primrose oil, soybean oil, sunflower seed oil, avocado oil, olive oil, sesame seed oil, coconut oil, arachis oil, castor oil, acetylated lanolin alcohols, petroleum jelly, mineral oil, butyl myristate, isostearic acid, palmitatic acid, isopropyl linoleate, lauryl lactate, myristyl lactate, decyl oleate, myristyl myristate;

Propellants, such as trichlorofluoromethane, dichlorodifluoromethane, dichlorotetrafluoroethane, monochlorodifluoromethane, trichlorotrifluoroethane, propane, butane, isobutane, dimethyl ether, carbon dioxide, nitrous oxide;

Solvents, such as ethyl alcohol, methylene chloride, isopropanol, acetone, ethylene glycol monoethyl ether, diethylene glycol monobutyl ether, diethylene glycol monoethyl ether, dimethyl sulphoxide, dimethyl formamide, tetrahydrofuran;

Powders, such as chalk, talc, fullers earth, kaolin, starch, gums, colloidal silica sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate.

The cosmetically acceptable vehicle will usually form from 10 to 99.9%, preferably from 50 to 99% by weight of the emulsion, and can, in the absence of other cosmetic adjuncts, form the balance of the composition.

OPTIONAL SKIN BENEFIT MATERIALS AND COSMETIC ADJUNCTS

A particularly convenient form of the composition according to the invention is an emulsion, in which case an oil or oily material will normally be present, together with an emulsifier to provide either a water-in-oil emulsion or an oil-in-water emulsion, depending largely on the average hydrophilic-lyophilic balance (HLB) of the emulsifier employed.

OIL OR OILY MATERIAL

The composition according to the invention can optionally comprise one or more oils or other materials having the properties of an oil.

Examples of suitable oils include mineral oil and vegetable oils, and oil materials, such as those already proposed herein as emollients. Other oils or oily materials include silicone oils, both volatile and non-volatile, such as polydimethyl siloxanes.

The oil or oily material, when present for the purposes for forming an emulsion, will normally form up to 90%, preferably from 10 to 80% by volume of the composition.

EMULSIFIER

The composition according to the invention can also optionally comprise one or more emulsifiers the choice of which will normally determine whether a water-in-oil or and oil-in-water emulsion is formed.

When a water-in-oil emulsion is required, the chosen emulsifier or emulsifiers should normally have an average HLB value of from 1 to 6. When an oil-in-water emulsion is required, a chosen emulsifier or emulsifiers should have an average HLB value of >6.

Examples of suitable emulsifiers are set below in Table 1 in which the chemical name of the emulsifiers is given together with an example of a trade name as commercially available, and the average HLB value.

TABLE 1

| Chemical Name of Emulsifier | Trade Name | HLB Value |
| --- | --- | --- |
| Sorbitan trioleate | Arlacel 85 | 1.8 |
| Sorbitan tristearate | Span 65 | 2.1 |
| Glycerol monooleate | Aldo MD | 2.7 |
| Glycerol monostearate | Atmul 84S | 2.8 |
| Glycerol monolaurate | Aldo MC | 3.3 |
| Sorbitan sesquioleate | Arlacel 83 | 3.7 |
| Sorbitan monooleate | Arlacel 80 | 4.3 |
| Sorbitan monostearate | Arlacel 60 | 4.7 |
| Poloxyethylene (2) stearyl ether | Brij 72 | 4.9 |
| Poloxyethylene sorbitol beeswax derivative | G-1702 | 5 |
| PEG 200 dilaurate | Emerest 2622 | 6.3 |
| Sorbitan monopalmitate | Arlacel 40 | 6.7 |
| Polyoxyethylene (3.5) nonyl phenol | Emulgen 903 | 7.8 |

TABLE 1-continued

| Chemical Name of Emulsifier | Trade Name | HLB Value |
| --- | --- | --- |
| PEG 200 monostearate | Tegester PEG 200 MS | 8.5 |
| Sorbitan monolaurate | Arlacel 200 | 8.6 |
| PEG 400 dioleate | Tegester PEG 400-DO | 8.8 |
| Polyoxyethylene (5) monostearate | Ethofat 60-16 | 9.0 |
| Polyoxyethylene (4) sorbitan monostearate | Tween 61 | 9.6 |
| Polyoxyethylene (4) lauryl ether | Brij 30 | 9.7 |
| Polyoxyethylene (5) sorbitan monooleate | Tween 81 | 10.0 |
| PEG 300 monooleate | Neutronyx 834 | 10.4 |
| Polyoxyethylene (20) sorbitan tristearate | Tween 65 | 10.5 |
| Polyoxyethylene (20) sorbitan trioleate | Tween 85 | 11.0 |
| Polyoxyethylene (8) monostearate | Myrj 45 | 11.1 |
| PEG 400 monooleate | Emerest 2646 | 11.7 |
| PEG 400 monostearate | Tegester PEG 400 | 11.9 |
| Polyoxyethylene 10 monooleate | Ethofat 0/20 | 12.2 |
| Polyoxyethylene (10) stearyl ether | Brij 76 | 12.4 |
| Polyoxyethylene (10) cetyl ether | Brij 56 | 12.9 |
| Polyoxyethylene (9.3) octyl phenol | Triton X-100 | 13.0 |
| Polyoxyethylene (4) sorbitan monolaurate | Tween 21 | 13.3 |
| PEG 600 monooleate | Emerest 2660 | 13.7 |
| PEG 1000 dilaurate | Kessco | 13.9 |
| Polyoxyethylene sorbitol lanolin derivative | G-1441 | 14.0 |
| Polyoxyethylene (12) lauryl ether | Ethosperse LA-12 | 14.4 |
| PEG 1500 dioleate | Pegosperse 1500 | 14.6 |
| Polyoxyethylene (14) laurate | Arosurf HFL-714 | 14.8 |
| Polyoxyethylene (20) sorbitan monostearate | Tween | 14.9 |
| Polyoxyethylene 20 sorbitan monooleate | Tween 80 | 15.0 |
| Polyoxyethylene (20) stearyl ether | Brij 78 | 15.3 |
| Polyoxyethylene (20) sorbitan monopalmitate | Tween 40 | 15.6 |
| Polyoxyethylene (20) cetyl ether | Brij 58 | 15.7 |
| Polyoxyethylene (25) oxypropylene monostearate | G-2162 | 16.0 |
| Polyoxyethylene (20) sorbitol monolaurate | Tween 20 | 16.7 |
| Polyoxyethylene (23) lauryl ether | Brij 35 | 16.9 |
| Polyoxyethylene (50) monostearate | Myrj 53 | 17.9 |
| PEG 4000 monostearate | Pegosperse 4000 MS | 18.7 |

The foregoing list of emulsifiers is not intended to be limiting and merely exemplifies selected emulsifiers which are suitable for use in accordance with the invention.

It is to be understood that two or more emulsifiers can be employed if desired.

The amount of emulsifier or mixtures thereof, to be incorporated in the composition of the invention, when appropriate is from 1 to 50%, preferably from 2 to 20% and most preferably from 2 to 10% by weight of the composition.

WATER

The composition of the invention can also comprise water, usually up to 80%, preferably from 5 to 80% by volume.

SILICONE SURFACTANT

The composition of the invention can also optionally comprise a high molecular weight silicone surfactant which can also act as an emulsifier, in place of or in addition to the optional emulsifier(s) already mentioned.

The silicone surfactant is a high molecular weight polymer of dimethyl polysiloxane with polyoxyethylene and/or polyoxypropylene side chains having a molecular weight of from 10,000 to 50,000 and having the structure:

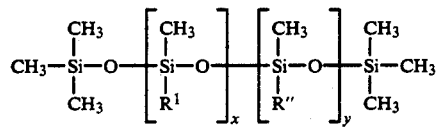

where the groups R' and R" are each chosen from —H, $C_{1-18}$ alkyl and

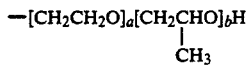

a has a value of from 9 to 115,
b has a value of from 0 to 50,
x has a value of from 133 to 673,
y has a value of from 25 to 0.25.

Preferably, the dimethyl polysiloxane polymer is one in which:
a has a value of from 10 to 114
b has a value of from 0 to 49
x has a value of from 38s to 402
y has a value of from 15 to 0.75
one of groups R' and R" being lauryl, and the other having a molcular weight of from 1,000 to 5,000.

A particular preferred dimethyl polysiloxane polymer is one in which:
a has the value 14
b has the value 13
x has the value 249
y has the value 1.25

The dimethyl polysiloxane polymer is conveniently provided as a dispersion in a volatile siloxane, the dispersion comprising, for example, from 1 to 20% by volume of the polymer and from 80 to 99% by volume of the volatile siloxane. Ideally, the dispersion consists of a 10% by volume of the polymer dispersed in the volatile siloxane.

Examples of the volatile siloxanes in which the polysiloxane polymer can be dispersed include polydimethyl siloxane (pentamer and/or hexamer).

A particularly preferred silicone surfactant is cyclomethicone and dimethicone copolyol, such as DC 3225C Formulation Aid available from DOW CORNING. Another is laurylmethicone copolyol, such as DC Q2-5200, also available from Dow Corning.

The amount of silicone surfactant, when present in the composition will normally be up to 25%, preferably from 0.5 to 15% by weight of the emulsion.

OTHER COSMETIC ADJUNCTS

Examples of conventional adjuncts which can optionally be employed include preservatives, such as para-hydroxy benzoate esters; antioxidants, such butyl hydroxy toluene; humectants, such as glycerol, sorbitol, 2-pyrrolidone-5-carboxylate, dibutylphthalate, gelatin, polyethylene, glycol, preferably PEG 200–600; buffers, such as lactic acid together with a base such as triethanolamine or sodium hydroxide; surfactants, such as glycerol ethers and other ceramides of synthetic, animal or plant origin; waxes, such as beeswax, ozokerite wax, paraffin wax, plant extracts, such as Aloe vera, cornflower, witch hazel, elderflower, cucumber; thickeners; activity enhancers; colourants; perfumes; and sunscreen materials such as ultrafine titanium dioxide and organic sunscreens such as p-aminobenzoic acid and esters thereof, ethylhexyl p-methoxycinnamate, 2-ethoxyethyl p-methoxycinnamate and butyl methoxydibenzoylmethane, and mixtures thereof.

In a further preferred composition, the amide derivative is combined with conventional ceramides, cholesterol, fatty acids and other ingredients well known to those skilled in the art to produce a liposomal dispersion.

In yet another preferred composition, the amide derivative is dissolved in squalene or squalane, optionally together with ceramides, and formulated with volatile and non-volatile silicones to produce an anhydrous or nearly anhydrous single phase system.

Cosmetic adjuncts can form the balance of the composition.

USE OF THE COMPOSITION

The composition according to the invention is intended primarily as a product for topical application to human skin, for treating dry or damaged skin to reduce moisture loss and to enhance the quality of skin. The composition can also be applied to hair.

In use, a small quantity of the composition, for example from 1 to 5 ml, is applied to exposed areas of the skin, from a suitable container or applicator and, if necessary, it is then spread over and/or rubbed into the skin using the hand or fingers or a suitable device.

PRODUCT FORM AND PACKAGING

The topical skin and/or hair treatment composition of the invention can be formulated as a lotion having a viscosity of from 4,000 to 10,000 mPas, a fluid cream having a viscosity of from 10,000 to 20,000 mPas or a cream having a viscosity of from 20,000 to 100,000 mPas, or above. The composition can be packaged in a suitable container to suit its viscosity and intended use by the consumer. For example, a lotion or fluid cream can be packaged in a bottle or a roll-ball applicator or a propellant-driven aerosol device or a container fitted with a pump suitable for finger operation. When the composition is a cream, it can simply be stored in a non-deformable bottle or squeeze container, such as a tube or a lidded jar.

The invention accordingly also provides a closed container containing a cosmetically acceptable composition as herein defined.

EXAMPLES

The invention is illustrated by the following examples.

EXAMPLE 1

This example illustrates a high internal phase water-in-oil emulsion in accordance with the invention.

A high internal phase water-in-oil emulsion having the following formulation was prepared:

|  | % w/w |
|---|---|
| Fully hydrogenated coconut oil | 3.9 |
| ω-(0-linoleoyl) acyl substituted amide having the structure (5) | 0.1 |
| Brij 92* | 5 |
| Bentone 38 | 0.5 |
| Preservative | 0.3 |
| MgSO$_4$7H$_2$O | 0.3 |
| Butylated hydroxy toluene | 0.01 |
| Perfume | qs |
| Water | to 100 |

*Brij 92 is polyoxyethylene (2) oleyl ether

EXAMPLE 2

This example also illustrates a high internal phase water-in-oil emulsion in accordance with the invention in which the formulation of Example 1 was prepared but with the following changes:
 i. liquid paraffin replaced the fully hydrogenated coconut oil, and
 ii the ω-(O-linoleoyl) acyl amide had the structure (6).

EXAMPLE 3

This example also illustrates a high internal phase water-in-oil emulsion in accordance with the invention in which the formulation of Example 1 was prepared but with the following changes:
The substituted amide had the structure (7).

EXAMPLE 4

This example illustrates an oil-in-water cream containing an ester of the invention.

An oil-in-water cream emulsion having the following formulation was prepared:

|  | % w/w |
|---|---|
| Mineral oil | 4 |
| ω-(0-linoleoyl) acyl substituted amide having the structure (5) | 0.1 |
| Brij 56* | 4 |
| Alfol 16RD* | 4 |
| Triethanolamine | 0.75 |
| Butane-1,3-diol | 3 |
| Xanthan gum | 0.3 |
| Preservative | 0.4 |
| Perfume | qs |
| Butylated hydroxy toluene | 0.01 |
| Water | to 100 |

*Brij 56 is cetyl alcohol POE (10)
Alfol 16RD is cetyl alcohol

EXAMPLE 5

This example also illustrates an oil-in-water emulsion containing an ester of the invention, in which the formulation of example 4 was prepared but with the following change:
the amide was an ω-(O-columbinoyl) (CH$_2$)$_{15}$ acyl substituted amide.

EXAMPLE 6

This example also illustrates an oil-in-water emulsion in accordance with the invention, in which the formulation of example 4 was prepared but with the following changes:
the amide was ω-(O-arachidonoyl) glucosyl acyl substituted amide).

EXAMPLE 7

This example illustrates an alcoholic lotion containing an amide of the invention.

The lotion had the following formulation:

|  | % w/w |
|---|---|
| ω-(0-linoleoyl) acyl substituted amide having the structure (5) | 0.2 |
| Ethanol | 40 |
| Perfume | qs |
| Butylated hydroxy toluene | 0.01 |
| Water | to 100 |

EXAMPLE 8

This example illustrates an alcoholic lotion containing an amide of the invention.

The lotion had the following formulations:

|  | % w/w |
|---|---|
| ω-(0-linoleoyl) acyl-substituted amide having the structure (6) | 0.2 |
| Dimethylsulphoxide | 10 |
| Ethanol | 40 |
| Antioxidant | 0.1 |
| Perfume | qs |
| Water | to 100 |

EXAMPLES 9 and 10

The following compositions according to the invention represent lotions which can be used in the treatment of dry skin:

|  | % w/w | |
|---|---|---|
|  | 9 | 10 |
| The amide derivative having the structure (7) | 1.5 | — |
| The amide, having the structure (5) | — | 0.5 |
| Perfume | 0.1 | 0.1 |
| Hydroxyethyl cellulose | 0.4 | 0.4 |
| Absolute ethanol | 25 | 25 |
| p-methyl benzoate | 0.2 | 0.2 |
| Sterilised demineralised water | to 100 | to 100 |

EXAMPLES 11 and 12

The following compositions according to the invention represent lotions which can be used in the treatment of dry skin:

|  | % w/w | |
|---|---|---|
|  | 11 | 12 |
| The amide derivative having the structure (6) | 0.08 | — |
| The amide having the structure (7) | — | 0.15 |
| Ethanol | 10 | 10 |
| Perfume | 0.5 | 0.5 |
| Distilled water | to 100 | to 100 |

I claim:
1. An amide derivative having the structure (1):

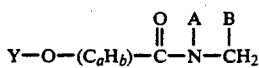  (1)

where Y is H or a residue of an all cis n-6,9 fatty acid or a derivative thereof, having the structure (2):

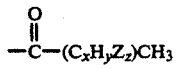  (2)

where Z is —OH or an epoxy oxygen
x is an integer of from 16 to 20
y is an integer of from 24 to 36, and
z is 0, or an integer of from 1 to 4;
provided that:
when z=0
then y is an integer from 26 to 36 or when z is an integer of from 1 to 4, then y is an integer of from 24 to 35;
and where
a is an integer of from 7 to 49
b is an integer of from 10 to 98
and where A is the group
—$(CH_2)_c$ OH, where c is an integer of from 1 to 6 or

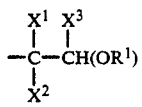  (3)

where $X^1$, $X^2$, and $X^3$ are individually H, $C_{1-5}$ alkyl or hydroxyalkyl, and $R^1$ is H, a sugar residue or a phosphate residue,
and where B is

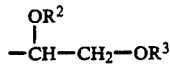  (4)

where
$R^2$ is H, a sugar residue or phosphate residue; and
$R^3$ is a $C_{8-28}$ aliphatic hydrocarbon or the group —CH(OH) $R^3$ with $R^3$ as defined above; and
wherein at least one of $R^1$ and $R^2$ must be a phosphate residue.

2. An amide derivative according to claim 1 wherein Y is a linoleoyl group.

3. An amide derivative according to claim 1 wherein Y is a linolenoyl group.

4. An amide derivative according to claim 1 wherein Y is a γ-linolenoyl group.

5. An amide derivative according to claim 1 wherein Y is a columbinoyl group.

6. An amide derivative according to claim 1 wherein Y is a arachidonoyl group.

7. A process for synthesising an amide derivative according to claim 1, which comprises the steps of:
 i. forming the acid chloride intermediate of a precursor having the structure (8):
  Y—O—$(C_aH_b)$—COOH;  (8)

ii. forming the silyl intermediate of an amine derivative having the structure (9):

$$\begin{array}{cc} A & B \\ | & | \\ HN\text{—}CH_2; \end{array}$$  (9)

iii. condensing the intermediates having structures (8) and (9); and
 iv. deprotecting by removal of the silyl groups to form the corresponding amide derivative having the structure (1):

Y—O—$(C_aH_b)$—C(=O)—N(A)—$CH_2$(B)  (1)

* * * * *